United States Patent
Ki Chul

(10) Patent No.: US 9,020,588 B2
(45) Date of Patent: Apr. 28, 2015

(54) BODY COMPOSITION ANALYZER FOR ANIMALS

(75) Inventor: Cha Ki Chul, Seoul (KR)

(73) Assignee: BioSpace Co., Ltd., Seoul (KR)

( * ) Notice: Subject to any disclaimer, the term of this patent is extended or adjusted under 35 U.S.C. 154(b) by 691 days.

(21) Appl. No.: 13/179,956

(22) Filed: Jul. 11, 2011

(65) Prior Publication Data
US 2012/0029380 A1 Feb. 2, 2012

(30) Foreign Application Priority Data

| Jul. 30, 2010 | (KR) | 10-2010-0074303 |
| Jul. 30, 2010 | (KR) | 10-2010-0074304 |
| Aug. 3, 2010 | (KR) | 10-2010-0075031 |

(51) Int. Cl.
A61B 5/00 (2006.01)
A61B 5/053 (2006.01)

(52) U.S. Cl.
CPC ............ *A61B 5/0537* (2013.01); *A61B 5/6829* (2013.01); *A61B 5/702* (2013.01); *A61B 2503/40* (2013.01); *A61B 2560/04* (2013.01)

(58) Field of Classification Search
CPC ... A61B 5/702; A61B 2503/40; A61B 5/6829
USPC ......................................... 600/547; 119/756
See application file for complete search history.

(56) References Cited

U.S. PATENT DOCUMENTS

| 5,794,570 | A * | 8/1998 | Foster et al. | 119/756 |
| 6,789,510 | B1 * | 9/2004 | Lee | 119/811 |
| 6,850,798 | B2 * | 2/2005 | Morgan et al. | 600/547 |
| 7,184,822 | B2 * | 2/2007 | Kasahara et al. | 600/547 |
| 7,357,421 | B2 * | 4/2008 | Locker et al. | 281/15.1 |
| 7,418,291 | B2 * | 8/2008 | Kasahara et al. | 600/547 |
| 2006/0278179 | A1 * | 12/2006 | Vasquez et al. | 119/864 |
| 2010/0012039 | A1 * | 1/2010 | Hallstrom | 119/14.02 |

FOREIGN PATENT DOCUMENTS

| JP | 2003144005 A | 5/2003 |
| JP | 2005160442 | 6/2005 |
| KR | 1020040085124 | 10/2004 |
| KR | 1020060000314 | 1/2006 |
| KR | 1020060089935 | 8/2006 |

OTHER PUBLICATIONS

Korean Office Action issued by Korean Patent Office on Aug. 30, 2011 for the corresponding Korean Patent Application No. 10-2010-0074303.

* cited by examiner

*Primary Examiner* — Brian Szmal
*Assistant Examiner* — H. Q. Nguyen
(74) *Attorney, Agent, or Firm* — Marshall, Gerstein & Borun LLP

(57) ABSTRACT

A body composition analyzer for animals is provided. A movement of an animal may be restrained by controlling a physical motion of a plurality of electrode units that come into contact with feet of the animal and thus, it is possible to effectively restrict the movement of the animal during measuring of a body composition of the animal, thereby more accurately measuring the body composition.

15 Claims, 21 Drawing Sheets

US 9,020,588 B2

BODY COMPOSITION ANALYZER FOR ANIMALS

CROSS-REFERENCE TO RELATED APPLICATIONS

This application claims the benefit of Korean Patent Application No. 10-2010-0074303 and Korean Patent Application No. 10-2010-0074304, filed on Jul. 30, 2010, and Korean Patent Application No. 10-2010-0075031, filed in Aug. 3, 2010, in the Korean Intellectual Property Office, the disclosures of which are incorporated herein by reference.

BACKGROUND

1. Field of the Invention

The present invention relates to a body composition analyzing technology, and more particularly, to a body composition analyzer for animals that may analyze a body composition of animals.

2. Description of the Related Art

Unlike people, it is difficult to accurately measure body composition of animals, such as dogs or cats, because animals tend to move frequently. Accordingly, to accurately measure the body composition of animals, such as dogs or cats, special measures are required to restrict movements of animals.

Therefore, researches have been conducted on a technology that may more accurately measure a body composition of an animal, such as a dog or a cat, by effectively restricting a movement of the animal during measuring of the body composition.

SUMMARY

An aspect of the present invention provides a body composition analyzer for animals that may effectively restrict a movement of an animal when a body composition of the animal is measured.

According to an aspect of the present invention, a body composition analyzer for animals may restrain a movement of an animal by controlling a physical motion of electrode units that come into contact with feet of the animal.

According to another aspect of the present invention, in a body composition analyzer for animals, electrode units that come into contact with feet of an animal may be installed to be spaced apart by a predetermined distance from the ground, so that the animal may be reluctant to move.

According to still another aspect of the present invention, a body composition analyzer for animals may restrain a movement of an animal using a visual means or auditory means, and may measure a body composition of the animal while the movement of the animal is restrained.

EFFECT

According to embodiments of the present invention, it is possible to effectively restrict a movement of an animal during measuring of a body composition of the animal, thereby more accurately measuring the body composition.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Figure 1:
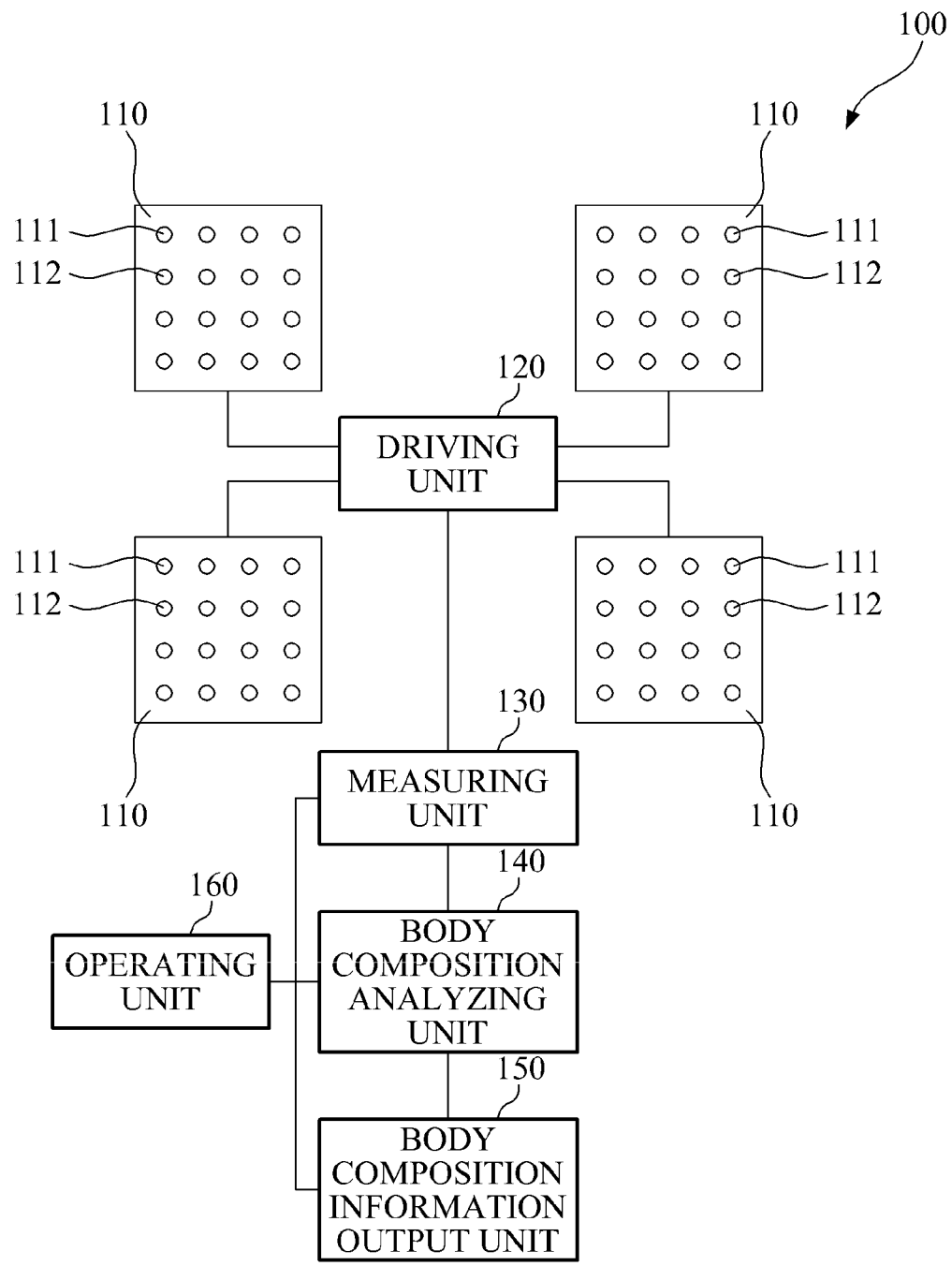
FIG. 1 is a block diagram illustrating a configuration of a body composition analyzer for animals according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

FIG. 1 is a block diagram illustrating a configuration of a body composition analyzer 100 for animals according to an embodiment of the present invention. In FIG. 1, the body composition analyzer 100 may include a plurality of electrode units 110, a driving unit 120, a measuring unit 130, and a body composition analyzing unit 140.

The electrode units 110 may each include at least one first electrode, for example a first electrode 111, and at least one second electrode, for example a second electrode 112 that come into contact with feet of an animal. The first electrode 111 may be used to apply a current to the feet of the animal, and the second electrode 112 may be used to measure a voltage applied to the animal.

The driving unit 120 may control physical motion of the plurality of electrode units 110, so that a movement of the animal may be restrained. In other words, the driving unit 120 may be configured to restrict the movement of the animal by the physical motion. For example, when the electrode units 110 in contact with the feet of the animal are physically moved by the driving unit 120, the animal may be reluctant to move due to habits of animals.

The measuring unit 130 may apply a current to a foot of the animal in contact with the first electrode 111, and may measure a voltage applied to a foot of the animal in contact with the second electrode 112, while the electrode units 110 are moved by the driving unit 120, that is, while the animal is reluctant to move. Accordingly, the measuring unit 130 may accurately measure a voltage applied to a living body of the animal when the animal does not move.

The body composition analyzing unit 140 may compute a biological impedance of the animal from the voltage measured by the measuring unit 130, and may analyze a body composition of the animal, for example a body fat percentage, from the computed biological impedance.

For example, when a current is applied to the animal through the first electrode 111 in contact with a left front foot and a left hind foot of the animal, and when a voltage is detected from the second electrode 112 in contact with the left front foot and a right hind foot of the animal, an impedance of a trunk of the animal may be obtained.

Since an impedance value of the trunk is more important than and is much smaller than those of legs of the animal, it is impossible to accurately analyze the body composition of the animal when the animal moves.

Accordingly, when the movement of the animal is physically restrained by physically moving the plurality of electrode units 110 in contact with the feet of the animal through the driving unit 120, an impedance applied to the trunk of the animal may be accurately measured by the measuring unit 130, and the measured impedance may be analyzed by the body composition analyzing unit 140. Thus, it is possible to accurately analyze the body composition.

Referring to FIG. 1, the body composition analyzer 100 may further include a body composition information output unit 150, and an operating unit 160.

The body composition information output unit 150 may output body composition information using a screen, a sound, a network, or printing, so that the body composition information may be provided to a user. Here, the body composition information may be analyzed by the body composition analyzing unit 140, and may include, for example, a body fat percentage of the animal and the like.

The operating unit 160 may be used as an interface for various user inputs, such as a command to start analyzing of a body composition, and the like. In other words, the operating unit 160 may enable user inputs. The operating unit 160 may be implemented, for example, as a key button.

Figure 2:
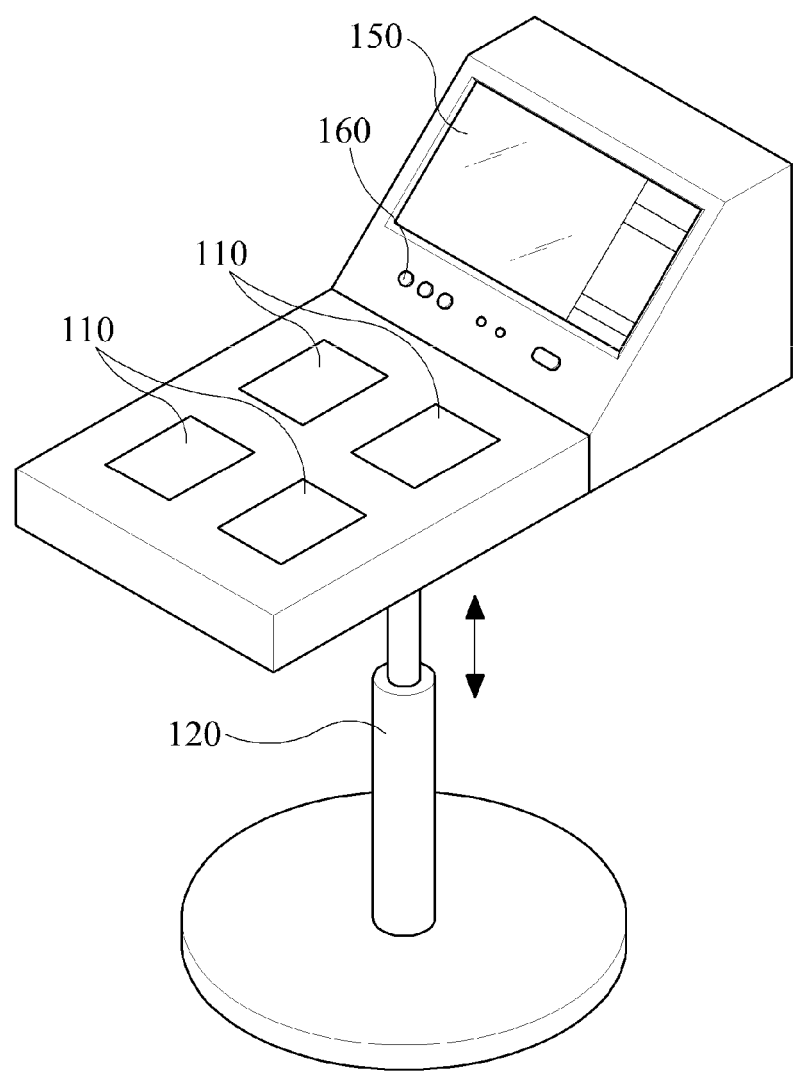
FIG. 2 is a diagram illustrating an example in which a plurality of electrode units of the body composition analyzer of FIG. 1 are simultaneously moved.

In an example, the physical motion may include a simultaneous movement of the electrode units 110. FIG. 2 is a diagram illustrating an example in which electrode units 110 are simultaneously moved.

As shown in FIG. 2, the electrode units 110 may be placed on a single substrate, and the substrate including the electrode units 110 may be moved by a driving unit 120, so that the electrode units 110 may be simultaneously moved. Here, the driving unit 120 may be implemented, for example, as a hydraulic cylinder enabling a reciprocating motion of the substrate.

Figure 3:
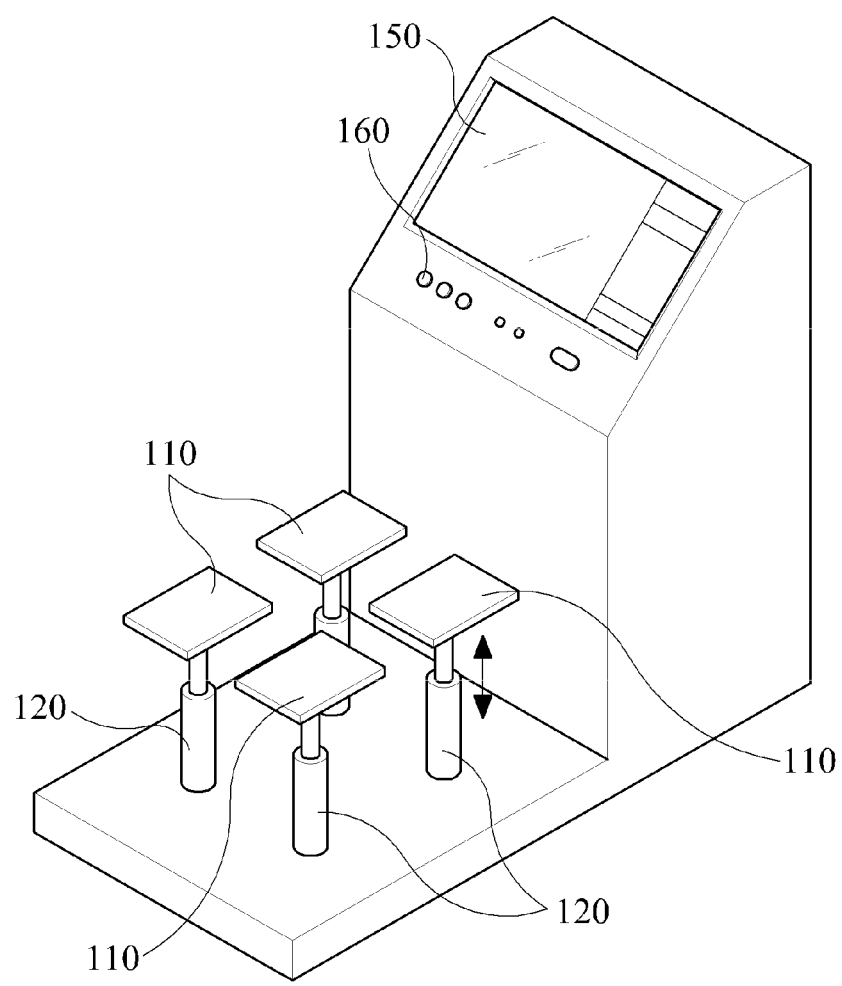
FIG. 3 is a diagram illustrating an example in which each of the electrode units is individually moved.

In another example, the physical motion may include an individual movement of each of the electrode units 110. FIG. 3 is a diagram illustrating an example in which each of electrode units 110 are individually moved.

As shown in FIG. 3, a plurality of substrates respectively including the electrode units 110 may be individually moved by a plurality of driving units 120, respectively. Here, each of the driving units 120 may be implemented, for example, as a hydraulic cylinder enabling a reciprocating motion of each of the substrates.

Figure 4:
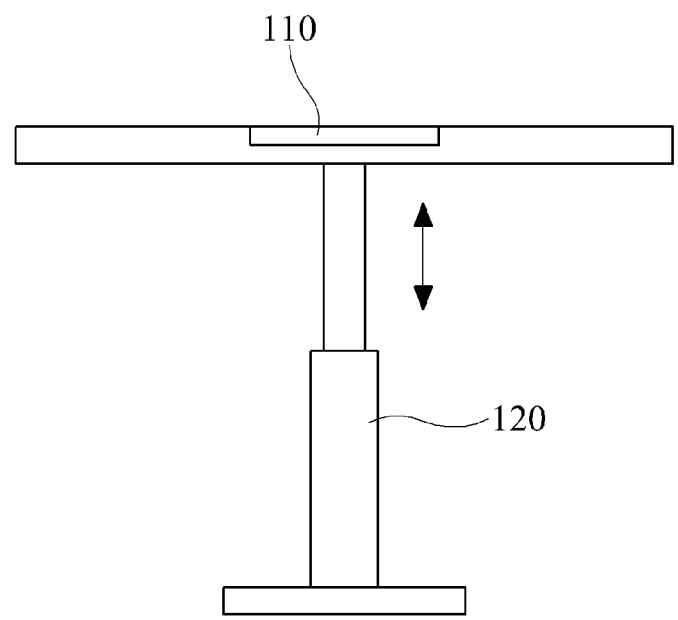
FIG. 4 is a diagram illustrating an example in which the electrode units are vertically moved.

In still another example, the physical motion may include a vertical movement of the electrode units 110. FIG. 4 is a diagram illustrating an example in which an electrode unit 110 is vertically moved.

As shown in FIG. 4, a substrate including the electrode unit 110 may be lifted and lowered by a driving unit 120. Here, the driving unit 120 may be implemented, for example, as a hydraulic cylinder enabling lifting and lowering of the substrate.

Figure 5:
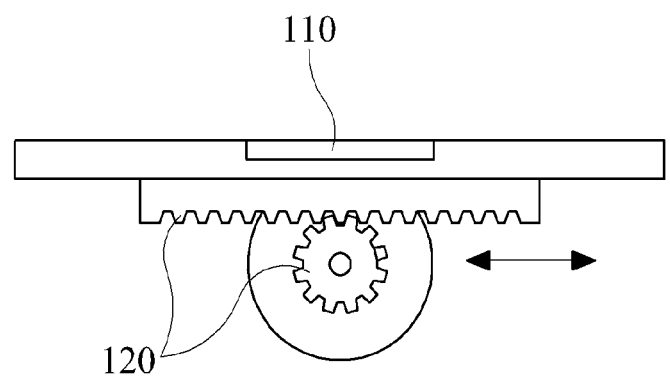
FIG. 5 is a diagram illustrating an example in which the electrode units are horizontally moved.

In yet another example, the physical motion may include a horizontal movement of the electrode units 110. FIG. 5 is a diagram illustrating an example in which an electrode unit 110 is horizontally moved.

As shown in FIG. 5, a substrate including the electrode unit 110 may be horizontally moved by a driving unit 120. For example, the driving unit 120 may include a rack, and a pinion gear. The rack may include the electrode unit 110, and the pinion gear may be rotated by a reversible motor and may enable a horizontal movement of the rack.

In a further example, the physical motion may include a movement of the electrode units 110 in a random direction. In the example of FIG. 3 in which the substrates respectively including the electrode units 110 are individually moved by the driving units 120, respectively, the driving units 120 may drive the substrates to move in different directions.

Figure 6:
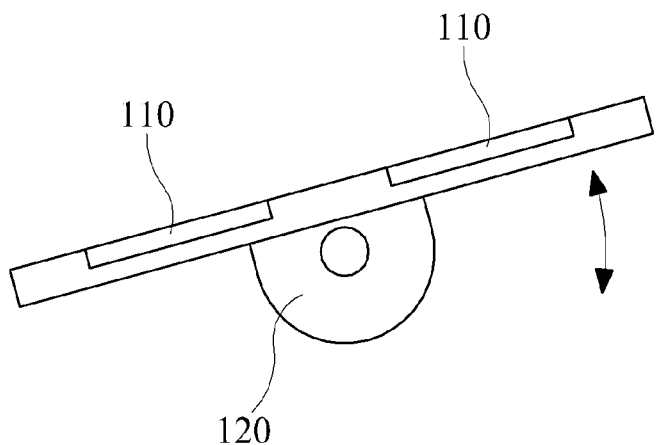
FIG. 6 is a diagram illustrating an example in which the electrode units are rotated.
Figure 7:
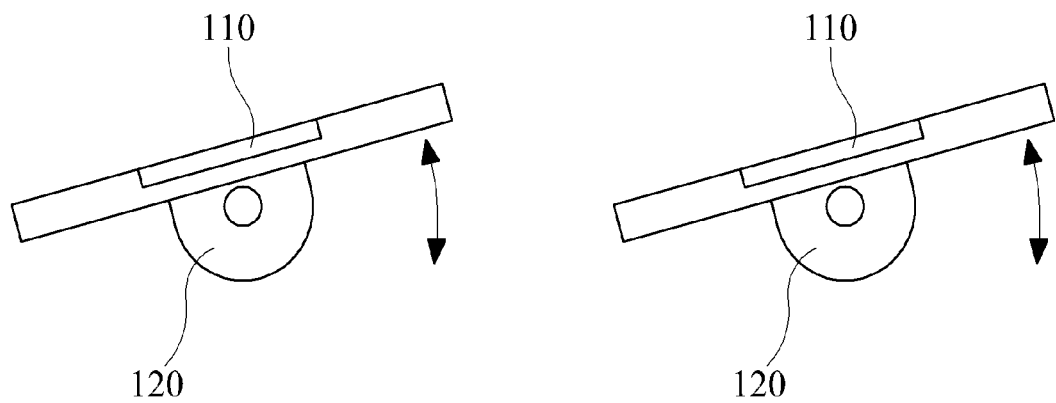
FIG. 7 is a diagram illustrating another example in which the electrode units are rotated.

In a further example, the physical motion may include a rotation of the electrode units 110. As shown in FIG. 6, a single substrate including electrode units 110 may be vertically rotated by a driving unit 120. Additionally, as shown in FIG. 7, a plurality of substrates respectively including electrode units 110 may be vertically rotated by a plurality of driving units 120, respectively. Here, the driving unit 120 for the rotation of the substrate including the electrode units 110 may be implemented, for example, as a reversible motor.

Figure 8:
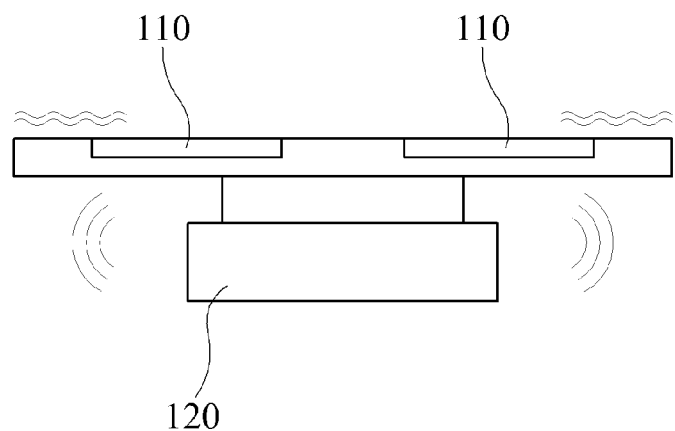
FIG. 8 is a diagram illustrating an example in which the electrode units are vertically vibrated.

In a further example, the physical motion may include a vibration of the electrode units 110. FIG. 8 is a diagram illustrating an example in which electrode units 110 are vertically vibrated.

As shown in FIG. 8, a substrate including the electrode units 110 may be vertically vibrated by a driving unit 120. Here, the driving unit 120 for the vibration of the substrate may be implemented, for example, as a piezo vibrating element.

According to an additional aspect of the present invention, as electrode units, facing each other, move closer to each other, a gap between the at least one first electrode, or a gap between the at least one second electrode may be narrowed.

Here, it is highly likely that a size of feet of an animal decreases, as a size of the animal decreases and accordingly, when the gap between the at least one first electrode or the gap between the at least one second electrode is adaptively implemented based on the size of the feet of the animal, it is possible to more easily measure a body composition of the animal.

Figure 9:
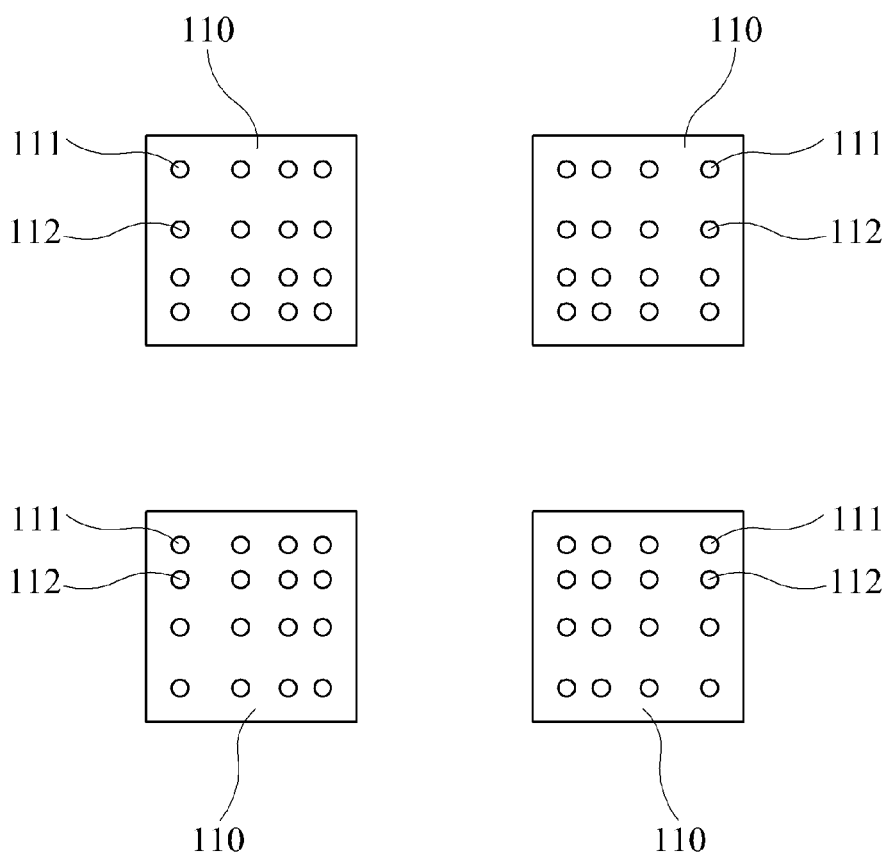
FIG. 9 is a diagram illustrating an example of an arrangement of electrodes in the electrode units.

FIG. 9 is a diagram illustrating an example of an arrangement of electrodes in electrode units. As shown in FIG. 9, as electrode units 110, facing each other, move closer to each other, a gap between first electrodes 111 or a gap between second electrodes 112 may be narrowed.

According to an additional aspect of the present invention, as electrode units, facing each other, move closer to each other, a size of the first electrode, or a size of the second electrode may be further reduced.

Here, it is highly likely that a size of feet of an animal decreases, as a size of the animal decreases and accordingly, when the size of the first electrode or the size of the second electrode is adaptively implemented based on the size of the feet of the animal, it is possible to more easily measure a body composition of the animal.

Figure 10:
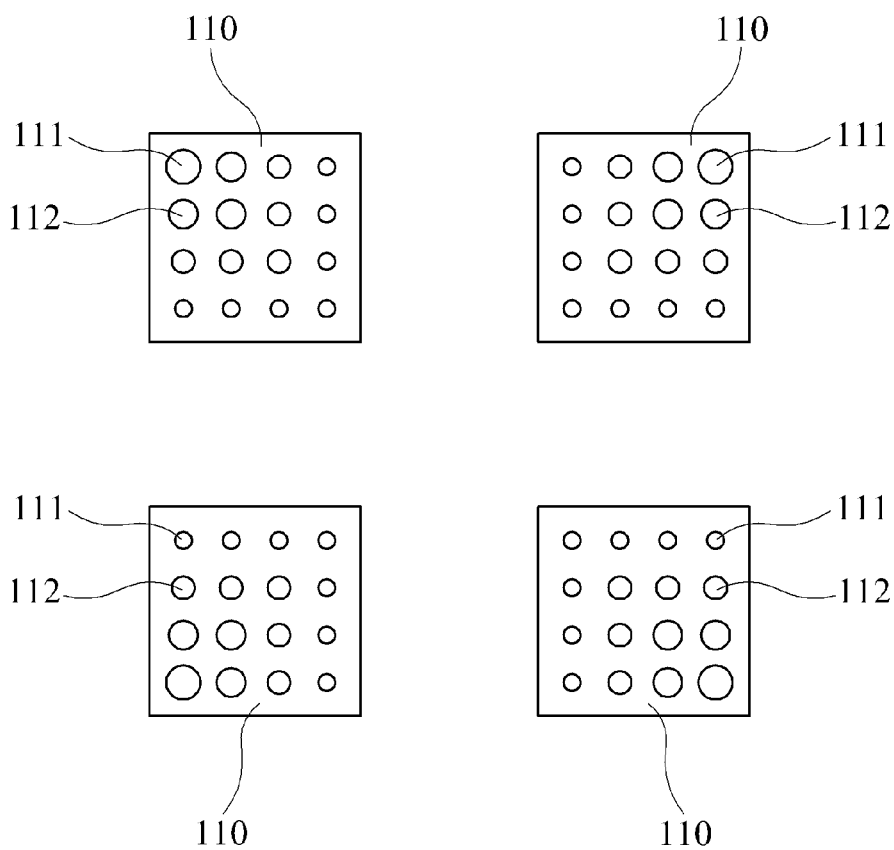
FIG. 10 is a diagram illustrating another example of an arrangement of electrodes in the electrode units.

FIG. 10 is a diagram illustrating another example of an arrangement of electrodes in electrode units. As shown in FIG. 10, as electrode units 110, facing each other, move closer to each other, first electrodes 111 or second electrodes 112 may be reduced in size.

Figure 11:
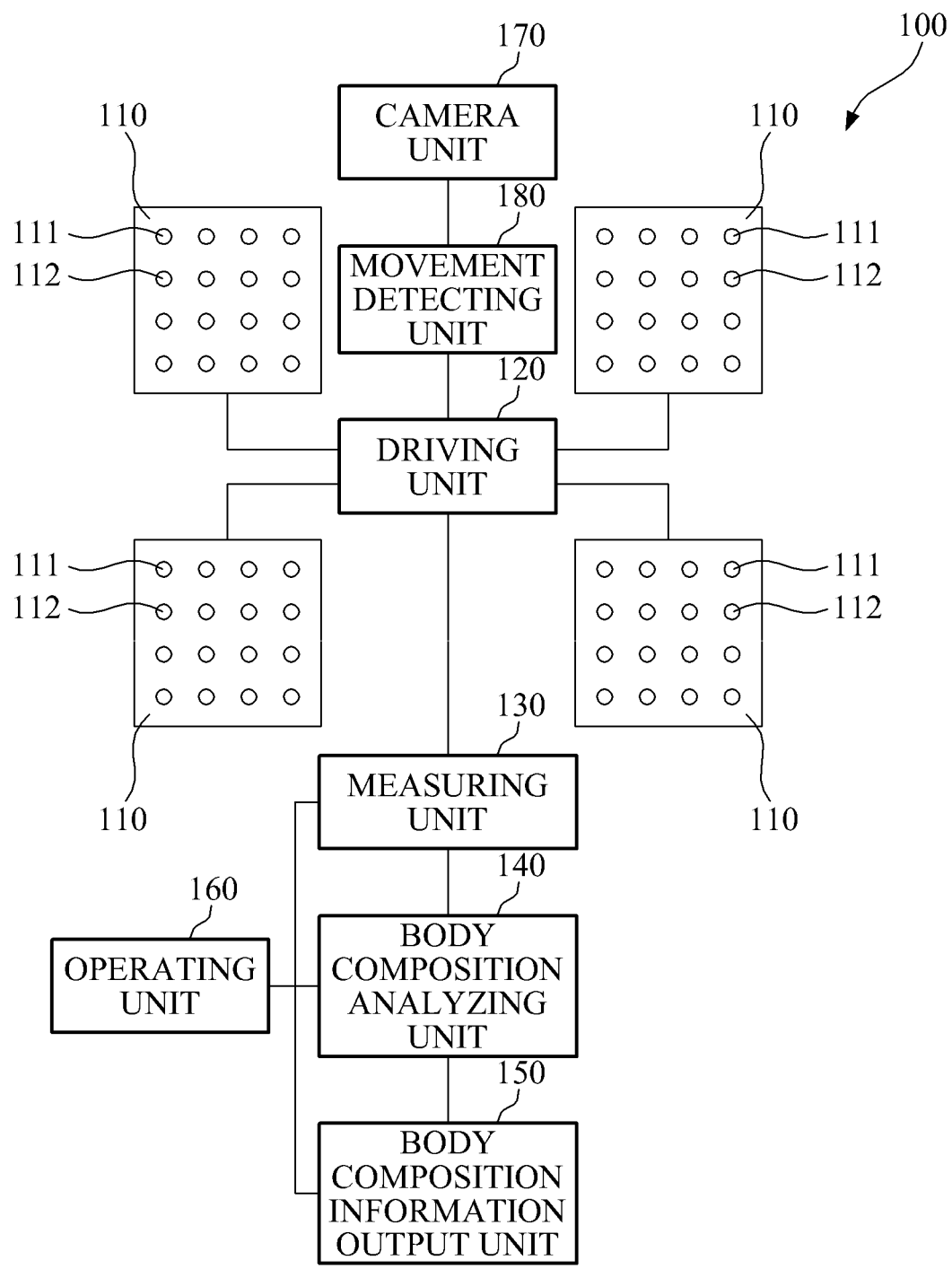
FIG. 11 is a block diagram illustrating a configuration of a body composition analyzer for animals according to another embodiment of the present invention.

According to an additional aspect of the present invention, the body composition analyzer 100 of FIG. 1 may further include a camera unit 170, and a movement detecting unit 180, as shown in FIG. 11. FIG. 11 is a block diagram illustrating a configuration of a body composition analyzer for animals according to another embodiment of the present invention.

The camera unit 170 may capture an animal image in real time. The movement detecting unit 180 may detect a movement of the animal from the animal image captured by the camera unit 170.

When the movement is detected by the movement detecting unit 180, the driving unit 120 may control the physical motion of the plurality of electrode units 110, so that the movement of the animal may be restrained.

Accordingly, the movement of the animal may be detected in real time, and the physical motion of the plurality of electrode units 110 in contact with the feet of the animal may be controlled adaptively based on the movement of the animal. Thus, it is possible to more accurately measure the body composition of the animal.

Figure 12:
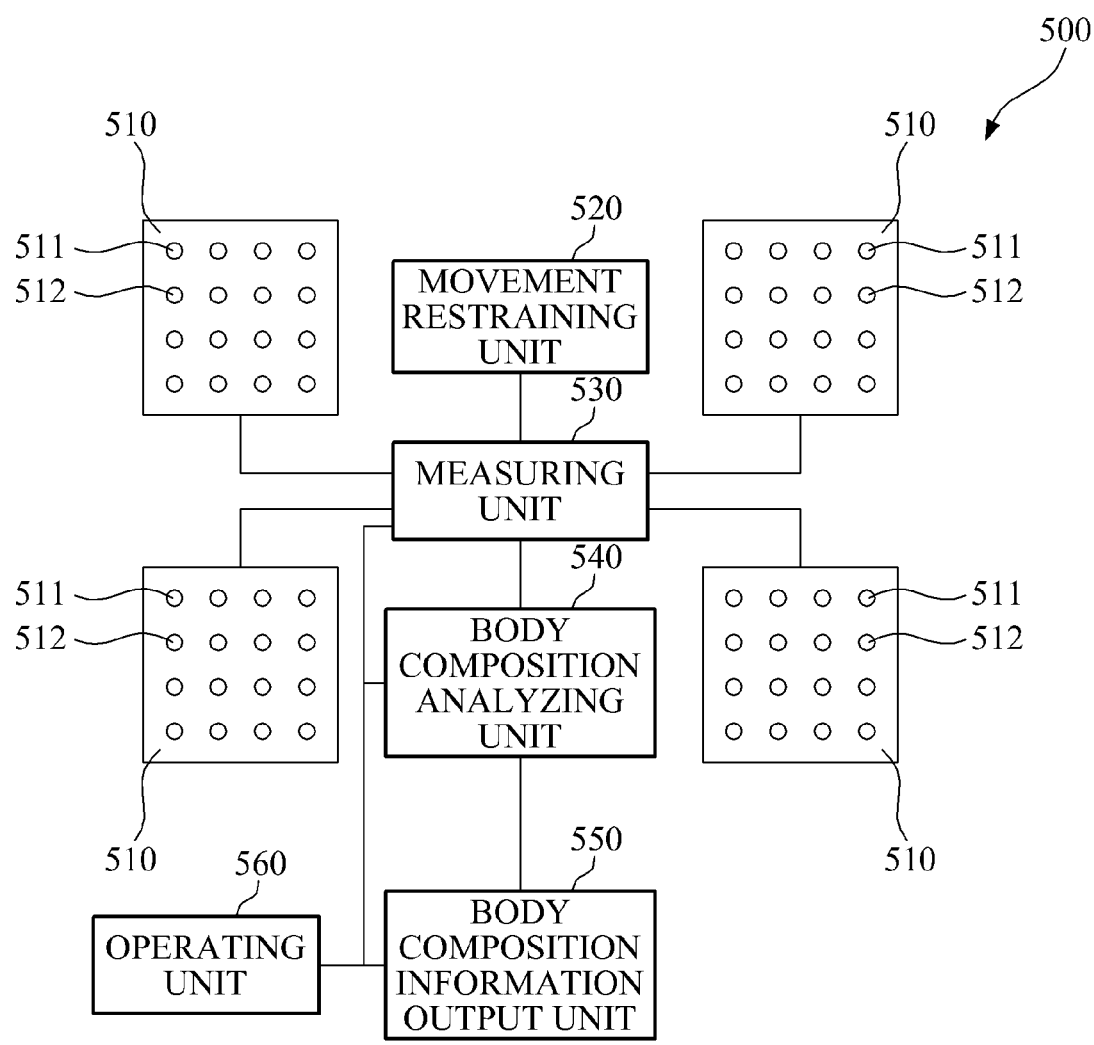
FIG. 12 is a block diagram illustrating a configuration of a body composition analyzer for animals according to still another embodiment of the present invention.

FIG. 12 is a block diagram illustrating a configuration of a body composition analyzer 500 for animals according to still another embodiment of the present invention. In FIG. 12, the body composition analyzer 500 may include a plurality of electrode units 510, a movement restraining unit 520, a measuring unit 530, and a body composition analyzing unit 540.

The plurality of electrode units 510 may each include at least one first electrode, for example a first electrode 511, and at least one second electrode, for example a second electrode 512 that come into contact with feet of an animal. The first electrode 511 may be used to apply a current to the feet of the animal, and the second electrode 512 may be used to measure a voltage applied to the animal.

The movement restraining unit 520 may visually or acoustically restrain a movement of the animal. In other words, the movement restraining unit 520 may be configured to restrict the movement of the animal using a visual means or auditory means, based on habits of animals that are reluctant to move when they visually or acoustically feel a fear or curiosity.

While the movement of the animal is restrained by the movement restraining unit 520, the measuring unit 530 may apply a current to a foot of the animal in contact with the first electrode 511, and may measure a voltage applied to a foot of the animal in contact with the second electrode 512. Accordingly, the measuring unit 530 may accurately measure the voltage applied to a living body of the animal when the animal does not move.

The body composition analyzing unit 540 may compute a biological impedance of the animal from the voltage measured by the measuring unit 530, and may analyze a body composition of the animal from the computed biological impedance.

For example, when a current is applied to the animal through the first electrode 511 in contact with a left front foot and a left hind foot of the animal, and when a voltage is detected from the second electrode 512 in contact with a left front foot and a right hind foot of the animal, an impedance of a trunk of the animal may be obtained.

Since an impedance value of the trunk is more important than and is much smaller than those of legs of the animal, it is impossible to accurately analyze the body composition of the animal when the animal moves.

Accordingly, when the movement of the animal is restrained by enabling the animal to feel a fear or curiosity using a visual means or auditory means, an impedance applied to the trunk of the animal may be accurately measured by the measuring unit 530, and the measured impedance may be analyzed by the body composition analyzing unit 540. Thus, it is possible to accurately analyze the body composition.

Additionally, the body composition analyzer 500 may further include a body composition information output unit 550, and an operating unit 560, as shown in FIG. 12.

The body composition information output unit 550 may output body composition information using a screen, a sound, a network, or printing, so that the body composition information may be provided to a user. Here, the body composition information may be analyzed by the body composition analyzing unit 540, and may include, for example, a body fat percentage of the animal and the like.

The operating unit 560 may be used as an interface for various user inputs, such as a command to start analyzing of a body composition, and the like. In other words, the operating unit 560 may enable user inputs. The operating unit 560 may be implemented, for example, as a key button.

In an example, the movement restraining unit 520 may be implemented as a transparent glass that is installed either between or below the electrode units 510, and that enables an animal to visually feel a fear or curiosity.

Figure 13:
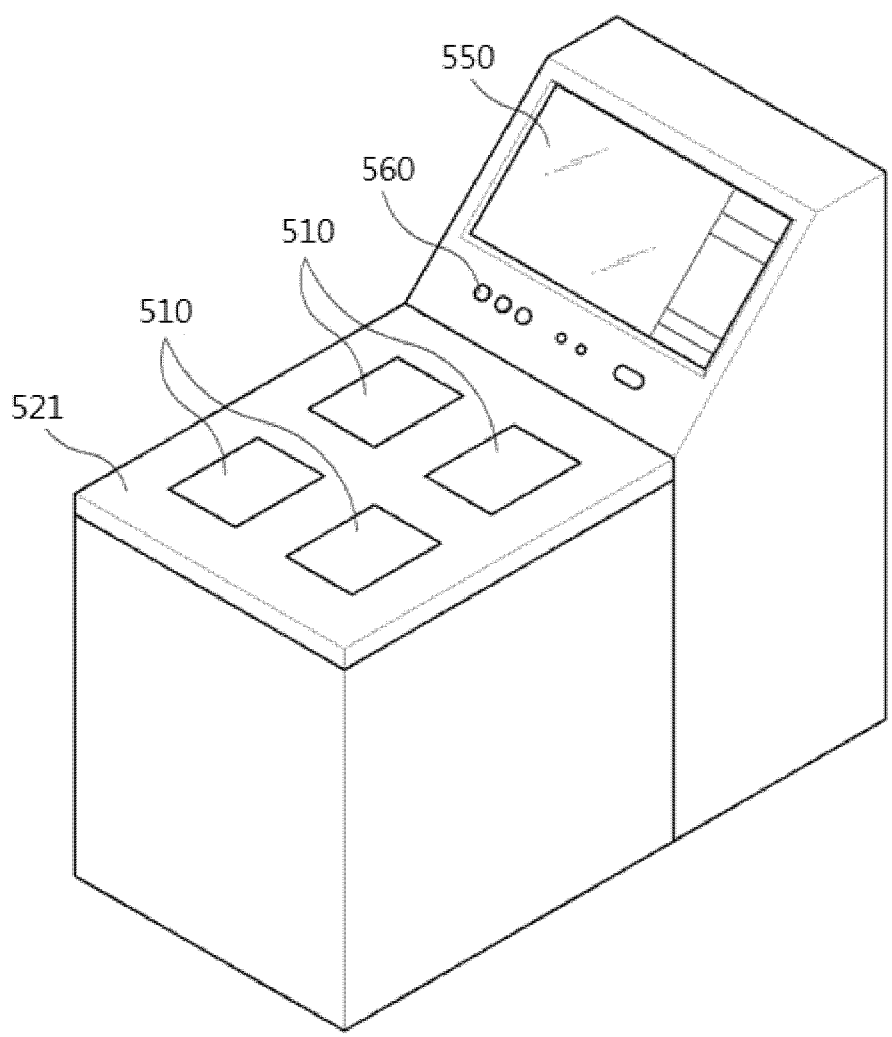
FIG. 13 is a diagram illustrating an example of employing a transparent glass as a movement restraining unit of the body composition analyzer of FIG. 12.

FIG. 13 is a diagram illustrating an example of employing a transparent glass as the movement restraining unit 520. As shown in FIG. 13, the electrode units 510 may be installed in a high position, and a transparent glass 521 may be installed between the electrode units 510, so that a bottom of the body composition analyzer 500 may be visible through the transparent glass 521. For example, when an animal in contact with the electrode units 510 looks down through the transparent glass 521, the animal may perceive the high position, and may feel a fear. Thus, it is possible to restrain a movement of the animal.

In another example, the movement restraining unit 520 may be implemented as a horizontal mirror that is installed either between or below the electrode units 510, and that enables an animal to visually feel a fear or curiosity.

Figure 14:
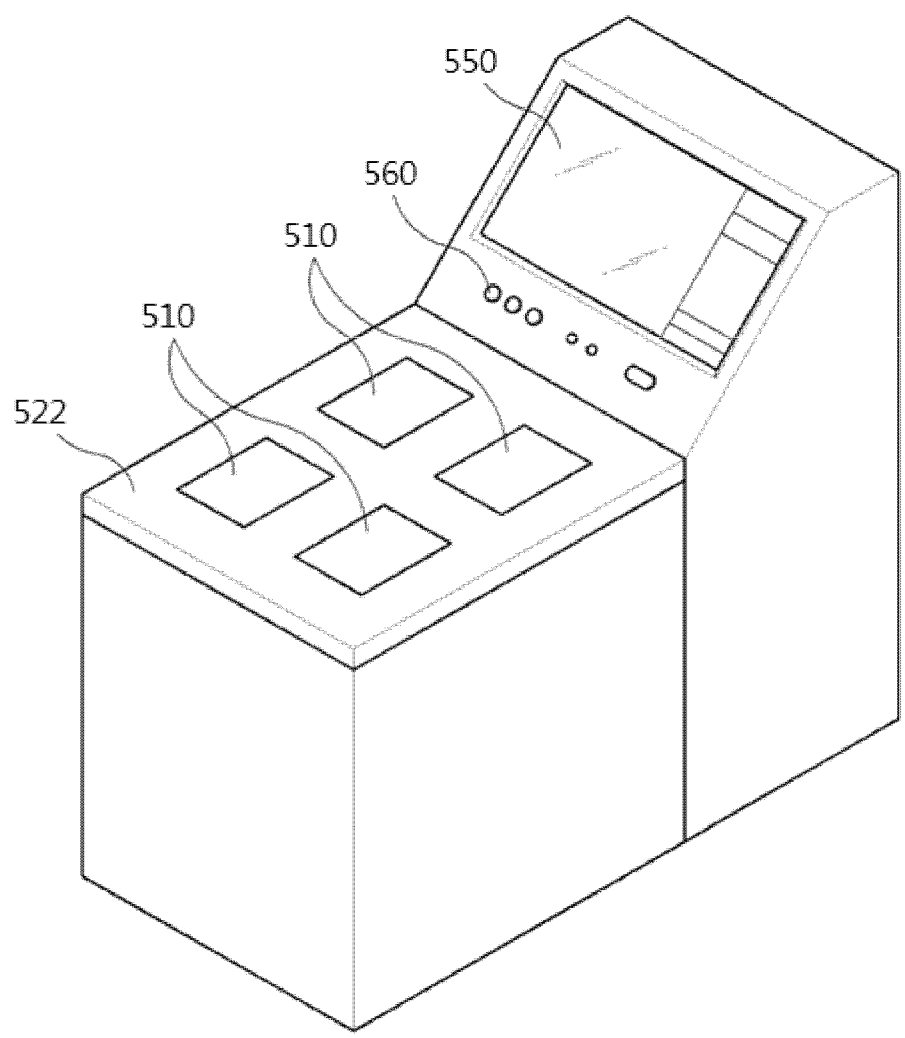
FIG. 14 is a diagram illustrating an example of employing a horizontal mirror as the movement restraining unit.

FIG. 14 is a diagram illustrating an example of employing a horizontal mirror as the movement restraining unit 520. As shown in FIG. 14, a horizontal mirror 522 may be installed between the electrode units 510, so that an appearance of an animal, the ceiling, and the like may be reflected in the horizontal mirror 522. For example, when an animal looks in the horizontal mirror 522, the animal may feel a curiosity or fear. Thus, it is possible to restrain a movement of the animal.

In still another example, the movement restraining unit 520 may be implemented as a vertical mirror that is installed in front of an animal in contact with the electrode units 510, and that enables the animal to visually feel a fear or curiosity.

Figure 15:
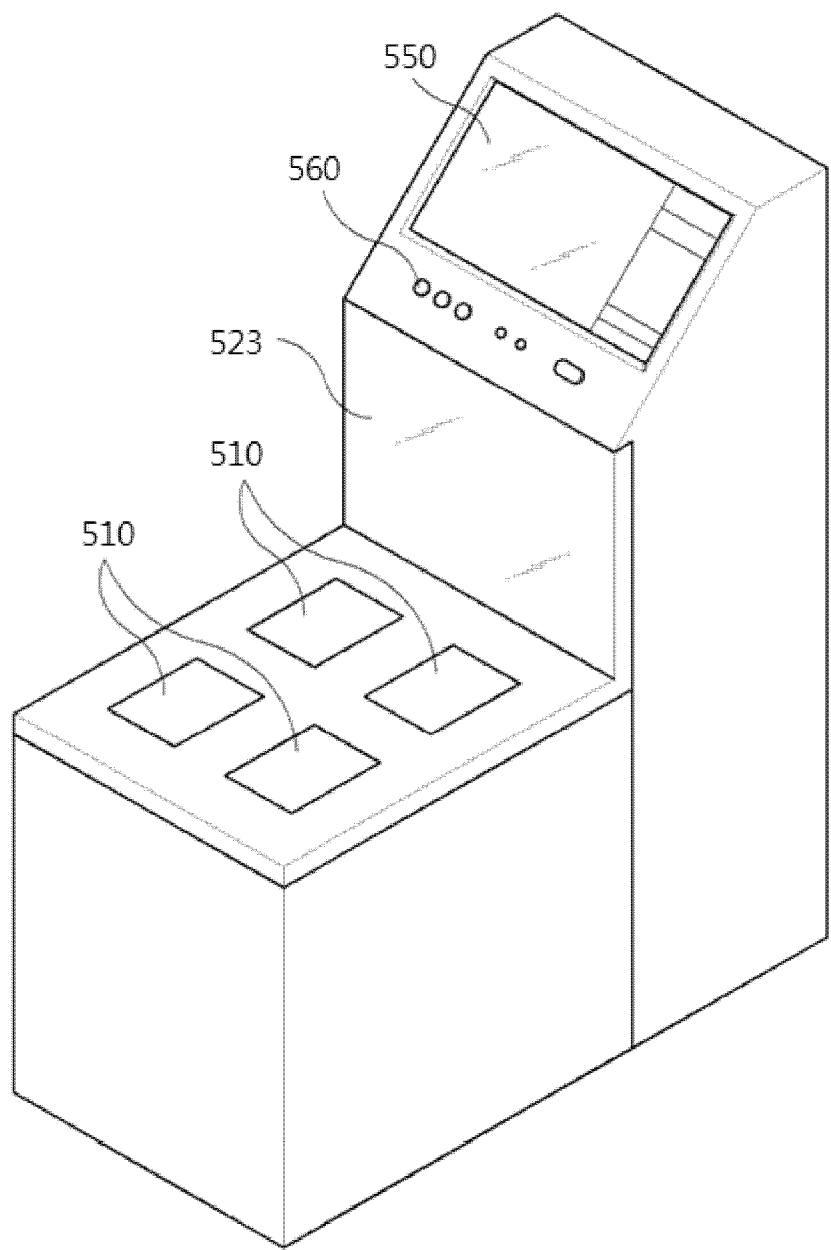
FIG. 15 is a diagram illustrating an example of employing a vertical mirror as the movement restraining unit.

FIG. 15 is a diagram illustrating an example of employing a vertical mirror as the movement restraining unit 520. As shown in FIG. 15, a vertical mirror 523 may be installed in front of an animal in contact with the electrode units 510, so that an appearance of the animal may be reflected in the vertical mirror 523. For example, when an animal looks in the vertical mirror 523, the animal may feel a curiosity. Thus, it is possible to restrain a movement of the animal.

In yet another example, the movement restraining unit 520 may be implemented as a light output device that is installed in front of an animal in contact with the electrode units 510, and that enables the animal to visually feel a fear or curiosity.

Figure 16:
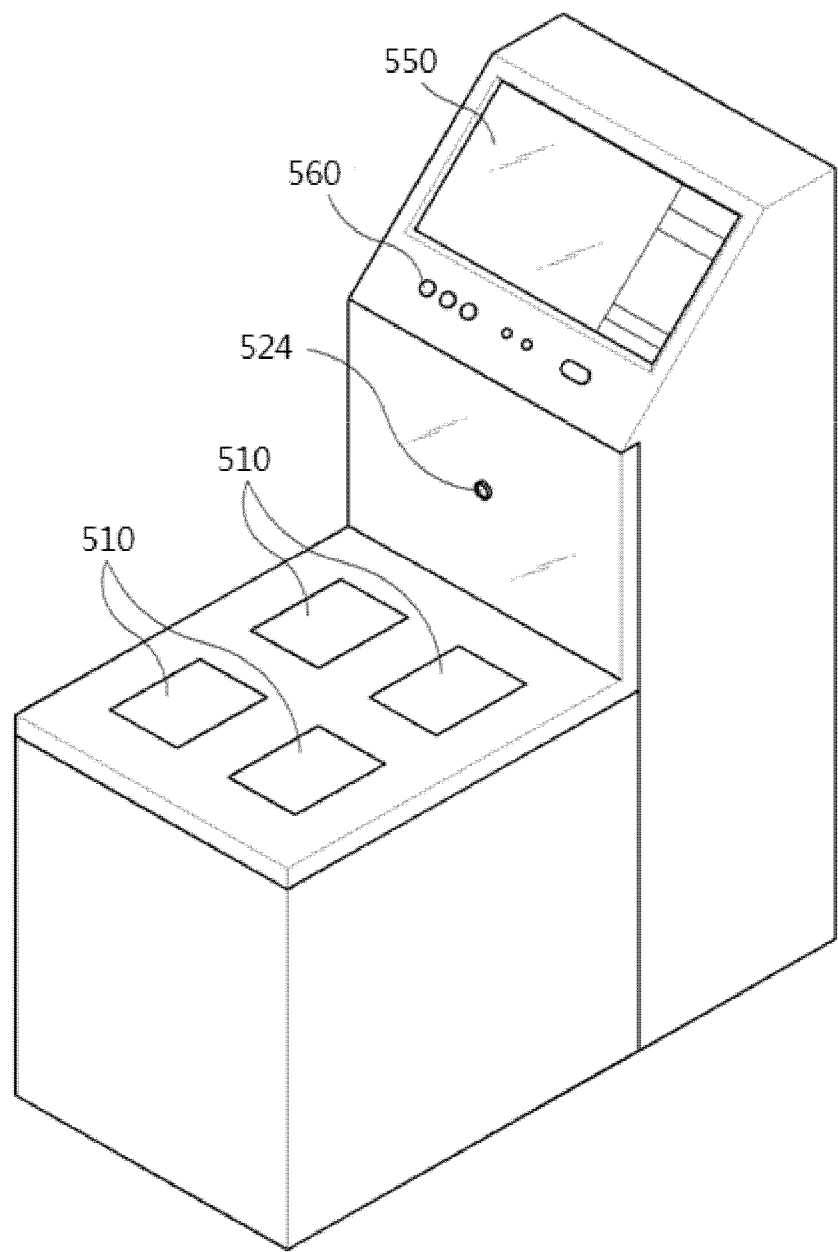
FIG. 16 is a diagram illustrating an example of employing a light output device as the movement restraining unit.

FIG. 16 is a diagram illustrating an example of employing a light output device as the movement restraining unit 520. As shown in FIG. 16, a light output device 524 may be installed in front of an animal in contact with the electrode units 510, and may stimulate a vision of the animal, so that the animal may feel a curiosity. Thus, it is possible to restrain a movement of the animal. Here, the light output device 524 may include, for example, a light emitting diode (LED) in which a light flickers with a short cycle.

In a further example, the movement restraining unit 520 may be implemented as a sound output device that outputs a sound enabling an animal to feel a fear or curiosity.

Figure 17:
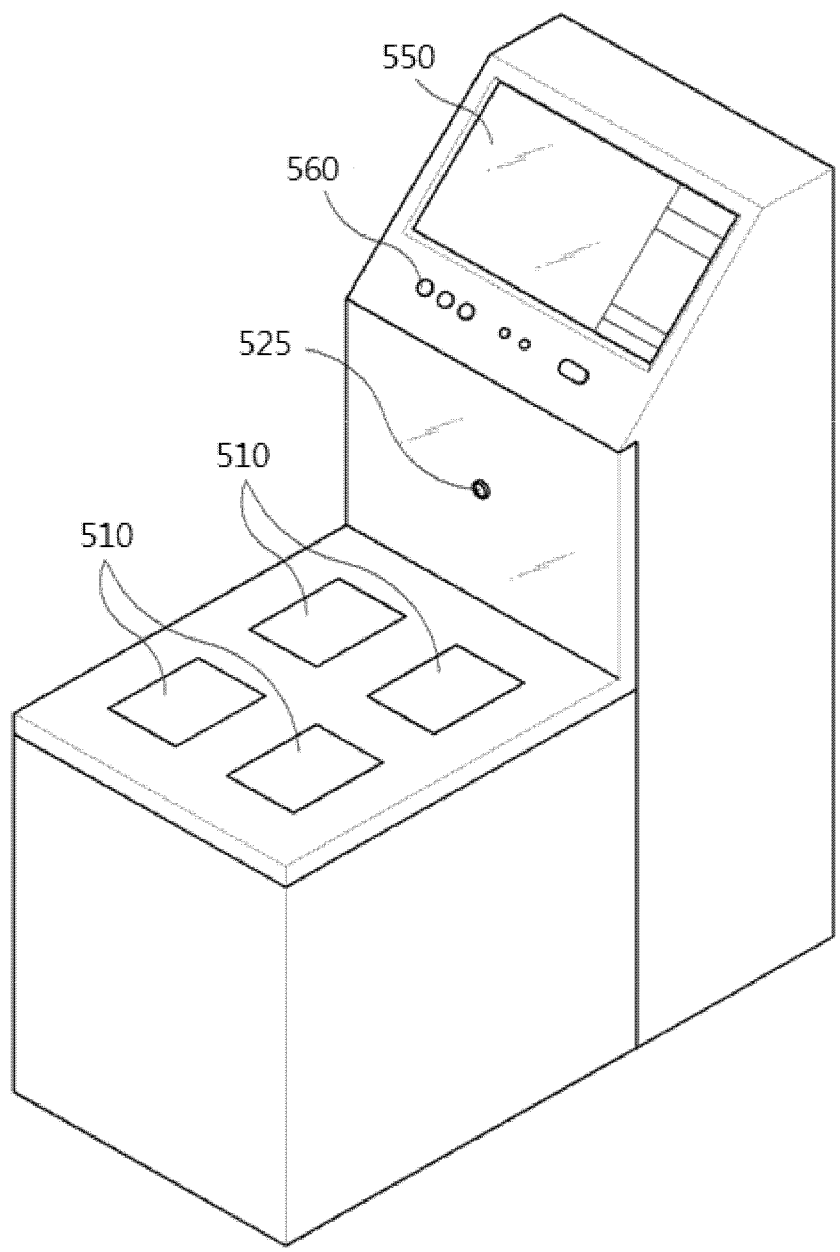
FIG. 17 is a diagram illustrating an example of employing a sound output device as the movement restraining unit.

FIG. 17 is a diagram illustrating an example of employing a sound output device as the movement restraining unit 520. As shown in FIG. 17, a sound output device 525, such as a speaker and the like, may output a sound enabling an animal to feel a curiosity, by stimulating an acoustic sense of the animal, and thus it is possible to restrain a movement of the animal.

Figure 18:
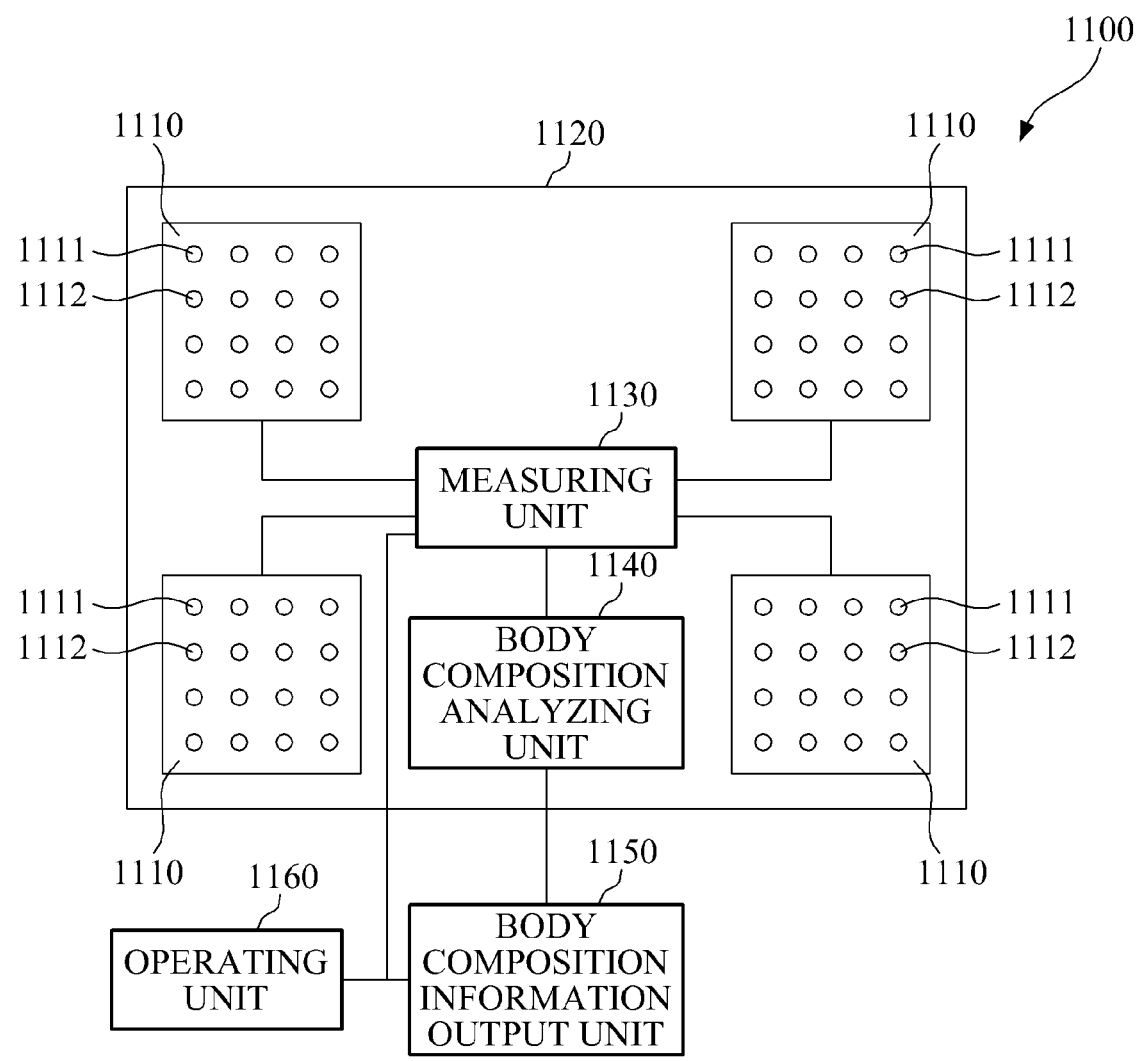
FIG. 18 is a block diagram illustrating a configuration of a body composition analyzer for animals according to yet another embodiment of the present invention.

FIG. 18 is a block diagram illustrating a configuration of a body composition analyzer 1100 for animals according to still another embodiment of the present invention.

In FIG. 18, the body composition analyzer 1100 may include a plurality of electrode units 1110, a support unit 1120, a measuring unit 1130, and a body composition analyzing unit 1140.

The plurality of electrode units 1110 may each include at least one first electrode, for example a first electrode 1111, and at least one second electrode, for example a second electrode 1112, that come into contact with feet of an animal. The electrode units 1110 may be spaced apart by a predetermined distance from the ground, so that the animal may be reluctant to move.

The first electrode 1111 may be used to apply a current to the feet of the animal, and the second electrode 1112 may be used to measure a voltage applied to the animal. When the first electrode 1111 and second electrode 1112 in contact with the feet of the animal are installed above the ground, the animal may be reluctant to move with a fear, due to habits of animals.

The support unit 1120 may be located below the electrode units 1110, and may support the electrode units 1110. The support unit 1120 may be implemented integrally with the electrode units 1110, or may be implemented detachably from the electrode units 1110. Additionally, the support unit 1120 may include a fixed leg with a specific length, or a length-adjustable leg.

The measuring unit 1130 may apply a current to a foot of the animal in contact with the first electrode 1111, and may measure a voltage applied to a foot of the animal in contact with the second electrode 1112. Accordingly, the measuring unit 1130 may accurately measure a voltage applied to a living body of the animal when the animal does not move.

The body composition analyzing unit 1140 may compute a biological impedance of the animal from the voltage measured by the measuring unit 1130, and may analyze a body composition of the animal from the computed biological impedance.

For example, when a current is applied to the animal through the first electrode 1111 in contact with a left front foot and a left hind foot of the animal, and when a voltage is detected from the second electrode 1112 in contact with the left front foot and a right hind foot of the animal, an impedance of a trunk of the animal may be obtained.

Since an impedance value of the trunk is more important than and is much smaller than those of legs of the animal, it is impossible to accurately analyze the body composition of the animal when the animal moves.

Accordingly, when an electrode unit in contact with a foot of an animal is spaced apart by a predetermined distance from the ground, the animal may be reluctant to move and thus, an impedance applied to the trunk of the animal may be accurately measured by the measuring unit 1130, and the measured impedance may be analyzed by the body composition analyzing unit 1140. Therefore, it is possible to accurately analyze the body composition.

Additionally, the body composition analyzer 1100 may further include a body composition information output unit 1150, and an operating unit 1160, as shown in FIG. 18.

The body composition information output unit 1150 may output body composition information using a screen, a sound, a network, or printing, so that the body composition information may be provided to a user. Here, the body composition information may be analyzed by the body composition analyzing unit 1140, and may include, for example, a body fat percentage of the animal and the like.

The operating unit 1160 may be used as an interface for various user inputs, such as a command to start analyzing of a body composition, and the like. In other words, the operating unit 1160 may enable user inputs. The operating unit 1160 may be implemented, for example, as a key button.

Figure 19:
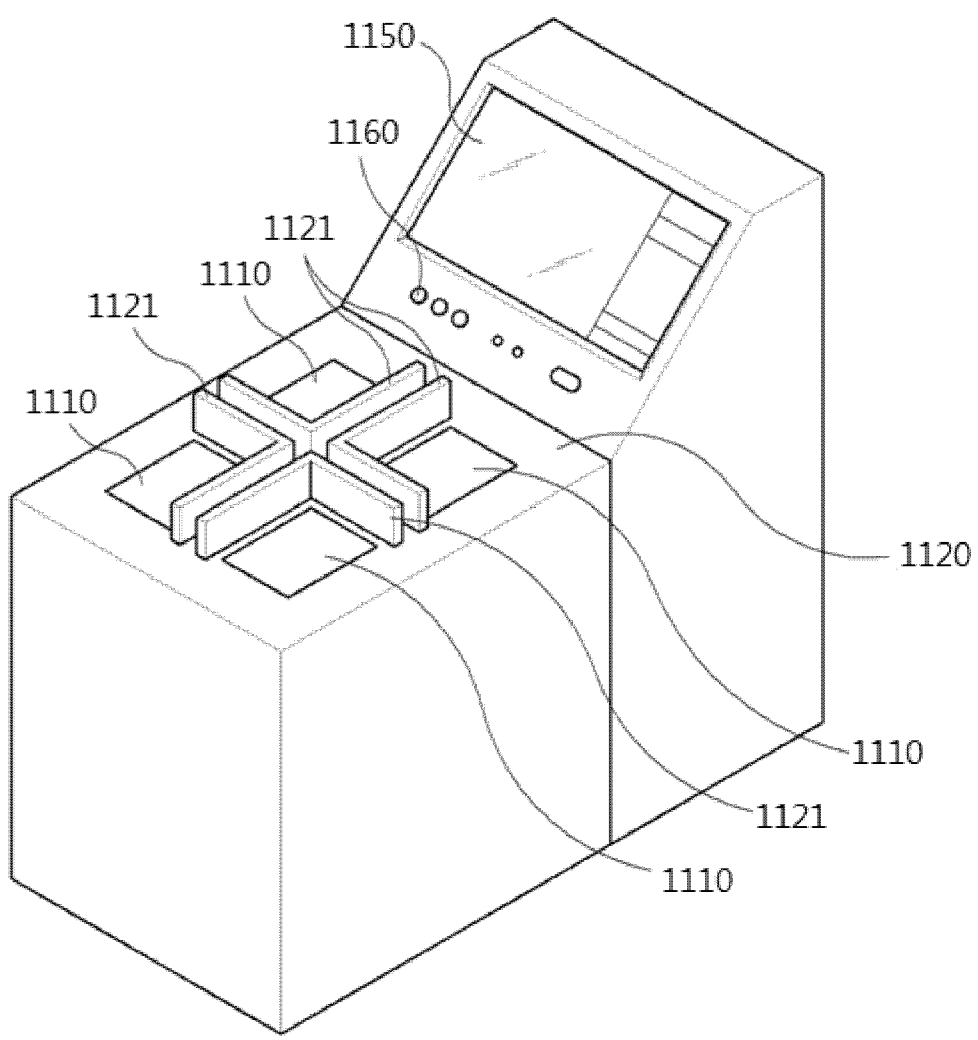
FIG. 19 is a diagram illustrating an example of the body composition analyzer of FIG. 18.

FIG. 19 is a diagram illustrating an example of the body composition analyzer 1100 of FIG. 18. As shown in FIG. 19, the support unit 1120 may include at least one movement obstructing partition, for example, a movement obstructing partition 1121. The movement obstructing partition 1121 may obstruct a movement of feet of an animal to a region in which two electrode units 1110 face each other.

For example, when the electrode units 1110 are spaced apart by a predetermined distance from the ground so that an animal is reluctant to move, and when four feet of the animal come into contact with the electrode units 1110, the animal may be scared and reluctant to move. However, in this example, the animal may escape from the electrode units 110 by moving legs of the animal.

Accordingly, the movement obstructing partition 1121 may be formed to obstruct the movement of the feet of the animal to the region in which the electrode units 1110 face each other, so that the feet of the animal may be prevented from escaping from the electrode units 1110 even when the animal moves the legs. Thus, it is possible to simply and accurately analyze a body composition of the animal.

Figure 20:
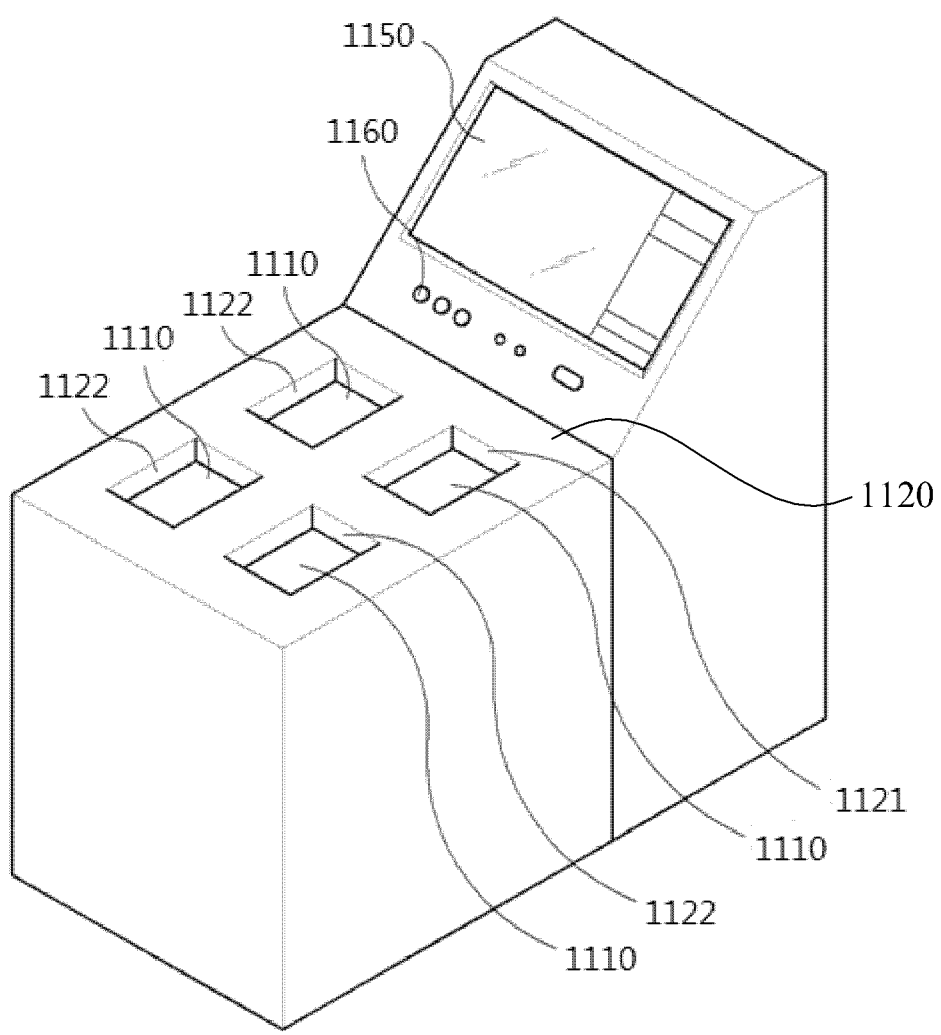
FIG. 20 is a diagram illustrating another example of the body composition analyzer of FIG. 18.

FIG. 20 is a diagram illustrating another example of the body composition analyzer 1100 of FIG. 18. As shown in FIG. 20, the support unit 1120 may include a plurality of grooves 1122. The electrode units 1110 may be installed in the grooves 1122, respectively, and the grooves 1122 may obstruct a movement of feet of an animal.

For example, when the electrode units 1110 are spaced apart by a predetermined distance from the ground so that an animal is reluctant to move, and when four feet of the animal come into contact with the electrode units 1110, the animal may be scared and reluctant to move. However, in this example, the animal may escape from the electrode units 110 by moving legs of the animal.

Accordingly, the grooves 1122 may be formed in the support unit 1120, and the electrode units 1110 may be respectively installed in the grooves 1122. When the feet of the animal come into contact with the electrode units 1110 in the grooves 1122, the feet of the animal may be naturally inserted into the grooves 1122, so that movement of the feet of the animal may be obstructed and the feet of the animal may be prevented from escaping from the electrode units 1110. Thus, it is possible to simply and accurately analyze a body composition of the animal.

Figure 21:
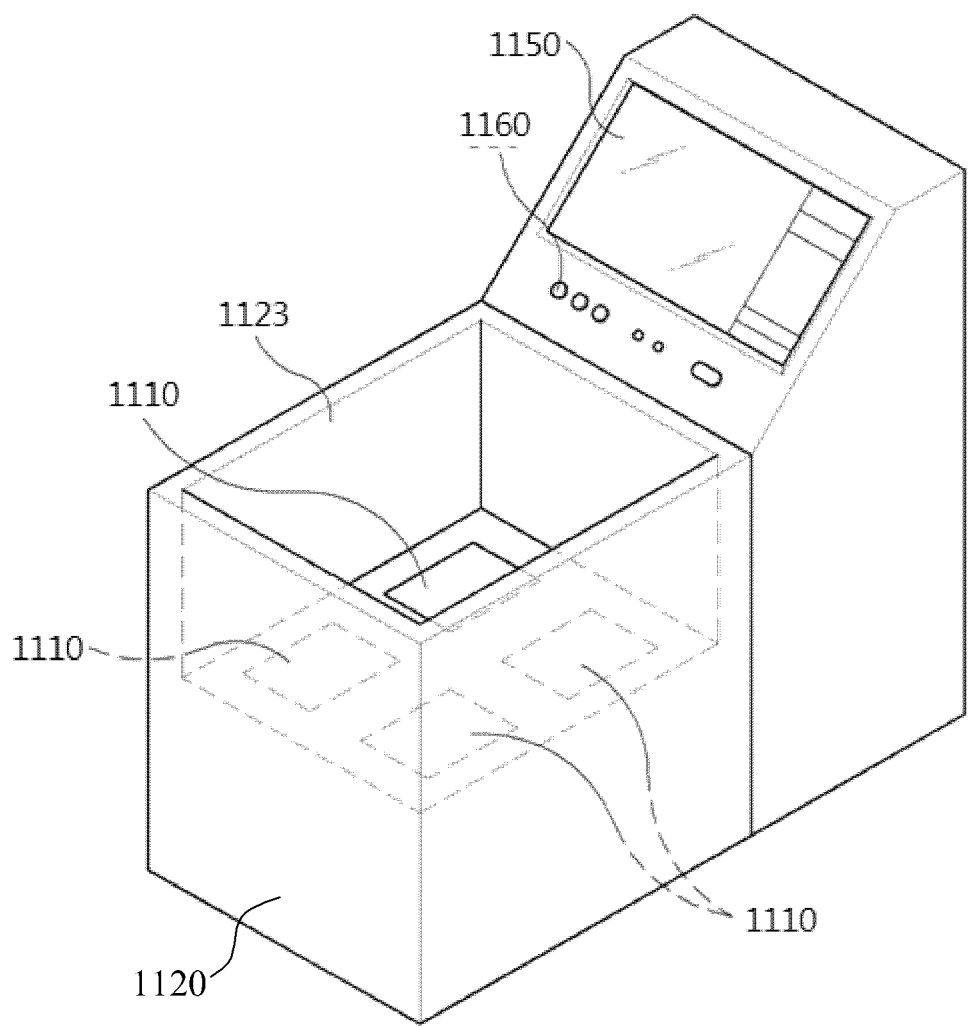
FIG. 21 is a diagram illustrating still another example of the body composition analyzer of FIG. 18.

FIG. 21 is a diagram illustrating still another example of the body composition analyzer 1100 of FIG. 18. As shown in FIG. 21, the support unit 1120 may include an escape preventing partition 1123 to prevent an animal from escaping from the body composition analyzer 1100.

For example, when the electrode units 1110 are spaced apart by a predetermined distance from the ground so that an animal is reluctant to move, and when four feet of the animal come into contact with the electrode units 1110, the animal may be scared and reluctant to move. However, in this example, the animal may jump to the ground.

Accordingly, the escape preventing partition 1123 may be installed around the support unit 1120, and may prevent the animal from jumping to the ground. Thus, it is possible to simply and accurately analyze a body composition of the animal.

As described above, according to embodiments of the present invention, it is possible to effectively restrict a movement of an animal by controlling a physical motion of a plurality of electrode units that come into contact with feet of the animal, during measuring of a body composition of the animal. Thus, it is possible to more accurately measure the body composition of the animal.

Additionally, according to embodiments of the present invention, it is possible to effectively restrict a movement of an animal using a visual means or auditory means, during measuring of a body composition of the animal. Thus, it is possible to more accurately measure the body composition of the animal.

Furthermore, according to embodiments of the present invention, electrode units that come into contact with feet of an animal may be installed to be spaced apart by a predetermined distance from the ground, so that the animal may be reluctant to move. Thus, it is possible to simply and accurately measure a body composition of an animal.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A body composition analyzer for a non-human animal, the body composition analyzer comprising:
   a plurality of moveable electrode units, each comprising at least one first electrode and at least one second electrode, the at least one first electrode configured to apply a current, the at least one second electrode configured to measure a voltage, and the at least one first electrode and the at least one second electrode configured to contact the feet of the non-human animal;
   a driving unit configured to move the plurality of moveable electrode units, wherein the driving unit is configured to control a physical motion of the plurality of moveable electrode units in contact with the feet of the non-human animal, the physical motion of the plurality of moveable electrode units selected to restrain movement of the non-human animal by inducing a reaction of stillness or reduced movement by the non-human animal in response to the physical motion of the plurality of moveable electrode units;
   a measuring unit to apply the current to a foot of the non-human animal in contact with the at least one first electrode, and to measure the voltage applied to a foot of the non-human animal in contact with the at least one second electrode, while the movement of the non-human animal is restrained in response to the physical motion of the plurality of moveable electrode units controlled by the driving unit; and
   a body composition analyzing unit configured to compute a biological impedance of the non-human animal from the voltage measured by the measuring unit, and to analyze a body composition of the non-human animal from the computed biological impedance.

2. The body composition analyzer of claim 1, wherein the physical motion comprises at least one of: a simultaneous movement of the plurality of moveable electrode units, an individual movement of each of the plurality of moveable electrode units, a vertical movement of the plurality of moveable electrode units, a horizontal movement of the plurality of moveable electrode units, a movement of the plurality of moveable electrode units in a random direction, a rotation of the plurality of moveable electrode units, or a vibration of the plurality of moveable electrode units.

3. The body composition analyzer of claim 1, wherein the plurality of moveable electrode units comprises a first electrode unit and a second electrode unit, the first electrode unit configured so that when the first and second electrode units, facing each other, move closer to each other, a gap narrows between (i) at least one first electrode of the first electrode unit and, (ii) at least one second electrode of the first electrode unit.

4. The body composition analyzer of claim 1, wherein the plurality of moveable electrode units comprises a first electrode unit and a second electrode unit, the first electrode unit configured so that when the first and second moveable electrode units, facing each other, move closer to each other, (i) a size of at least one first electrode of the first electrode unit is reduced, or (ii) a size of at least one second electrode is further reduced.

5. The body composition analyzer of claim 1, further comprising:
   a camera unit configured to capture an animal image in real time; and
   a movement detecting unit configured to detect the movement of the non-human animal from the animal image captured in real time by the camera unit,
   wherein the driving unit is configured to move the plurality of moveable electrode units so that the movement of the non-human animal is restrained, while the movement is detected by the movement detecting unit.

6. The body composition analyzer of claim 1, further comprising:

a support unit formed below the plurality of moveable electrode units and configured to support the plurality of moveable electrode units, so that the plurality of moveable electrode units are spaced apart by a predetermined distance from the ground and that the non-human animal is reluctant to move.

7. The body composition analyzer of claim 6, wherein the support unit comprises a movement obstructing partition configured to obstruct a movement of the feet of the non-human animal to a region in which two electrode units from the plurality of moveable electrode units face each other.

8. The body composition analyzer of claim 6, wherein the support unit comprises a plurality of grooves configured to obstruct a movement of the feet of the non-human animal, the plurality of moveable electrode units being respectively installed in the plurality of grooves.

9. The body composition analyzer of claim 6, wherein the support unit comprises an escape preventing partition configured to prevent the non-human animal from escaping from the body composition analyzer.

10. The body composition analyzer of claim 1, further comprising a movement restraining unit configured to provide visual or acoustical stimuli selected to restrain the movement of the non-human animal.

11. The body composition analyzer of claim 10, wherein the movement restraining unit comprises a transparent glass installed either between or below the plurality of moveable electrode units, the transparent glass configured to create a visual stimulus selected to deter movement by the non-human animal.

12. The body composition analyzer of claim 10, wherein the movement restraining unit driving unit comprises a horizontal minor installed either between or below the plurality of moveable electrode units, the horizontal mirror configured to create a visual stimulus selected to deter movement by the non-human animal.

13. The body composition analyzer of claim 10, wherein the movement restraining unit comprises a vertical mirror installed in front of the non-human animal having the feet in contact with the plurality of moveable electrode units, the vertical mirror configured to create a visual stimulus selected to deter movement by the non-human animal.

14. The body composition analyzer of claim 10, wherein the movement restraining unit comprises a light output device that is installed in front of the non-human animal having the feet in contact with the plurality of moveable electrode units, the light output device configured to create a visual stimulus selected to deter movement by the non-human animal.

15. The body composition analyzer of claim 10, wherein the movement restraining unit comprises a sound output device to output a sound selected to deter movement by the non-human animal.

* * * * *